US009883671B2

(12) United States Patent
Gradtke et al.

(10) Patent No.: US 9,883,671 B2
(45) Date of Patent: Feb. 6, 2018

(54) MIXTURE OF NATURAL OR NATURE-IDENTICAL ALCOHOLS WITH IMPROVED EFFECTIVENESS

(71) Applicant: L'AIR LIQUIDE, SOCIETE ANONYME POUR L'ETUDE ET L'EXPLOITATION DES PROCEDES, Paris (FR)

(72) Inventors: Ralf Gradtke, Tornesch (DE); Klaus Weber, Hamburg (DE); Wolfgang Beilfuss, Hamburg (DE); Stefan Sakulowski, Hamburg (DE)

(73) Assignee: L'AIR LIQUIDE, SOCIETE ANONYME POUR L'ETUDE ET L'EXPLOITATION DES PROCEDES GEORGES CLAUDE, Paris (FR)

( * ) Notice: Subject to any disclaimer, the term of this patent is extended or adjusted under 35 U.S.C. 154(b) by 0 days.

(21) Appl. No.: 14/414,463

(22) PCT Filed: Jun. 26, 2013

(86) PCT No.: PCT/EP2013/063372
§ 371 (c)(1),
(2) Date: Jan. 13, 2015

(87) PCT Pub. No.: WO2014/009157
PCT Pub. Date: Jan. 16, 2014

(65) Prior Publication Data
US 2015/0189872 A1 Jul. 9, 2015

(30) Foreign Application Priority Data
Jul. 13, 2012 (DE) .......................... 10 2012 212 281

(51) Int. Cl.
*A01N 31/02* (2006.01)
*A01N 31/04* (2006.01)

(52) U.S. Cl.
CPC ............. *A01N 31/04* (2013.01); *A01N 31/02* (2013.01)

(58) Field of Classification Search
CPC ........ A01N 31/02; A01N 31/04; A01N 31/08; A01N 31/14
USPC ........................................ 514/730, 738, 724
See application file for complete search history.

(56) References Cited

U.S. PATENT DOCUMENTS

| 5,539,001 A * | 7/1996 | Waldmann-Laue ... A01N 31/04 514/723 |
| 6,428,767 B1 | 8/2002 | Burch et al. |
| 2005/0154067 A1 * | 7/2005 | Beilfuss ................ A01N 31/02 514/715 |
| 2006/0110810 A1 | 5/2006 | Rajgarhia et al. |
| 2013/0230609 A1 * | 9/2013 | Modak .................. A01N 65/44 424/739 |

FOREIGN PATENT DOCUMENTS

| CA | 2327394 | * | 10/2000 | ............. A01N 31/02 |
| DE | 4140474 A1 | | 6/1993 | |
| DE | 4240674 C1 | | 3/1994 | |
| DE | 19831288 A1 | | 1/2000 | |
| DE | 69607178 T2 | | 12/2000 | |
| DE | 10224979 A1 | | 3/2003 | |
| DE | 69911388 T2 | | 6/2004 | |
| DE | 102004056362 A1 | | 6/2006 | |
| DE | 102005043188 A1 | | 3/2007 | |
| DE | 102006051891 A1 | | 5/2008 | |
| DE | 102009022445 A1 | | 12/2009 | |
| DE | 102009013469 A1 | | 12/2010 | |
| EP | 0524548 A1 | | 1/1993 | |
| EP | 0599433 A1 | | 6/1994 | |
| EP | 1206933 A1 | | 5/2002 | |
| JP | 2004182639 | * | 7/2004 | ............... A61K 7/48 |
| JP | 2005015401 A | | 1/2005 | |
| WO | 0189465 A2 | | 11/2001 | |
| WO | 0242471 A2 | | 5/2002 | |
| WO | 03069994 A1 | | 8/2003 | |
| WO | 2004062600 A2 | | 7/2004 | |
| WO | 2005009510 A2 | | 2/2005 | |
| WO | 2006068276 A1 | | 6/2006 | |
| WO | 2006082151 A2 | | 8/2006 | |
| WO | 2006134160 A2 | | 12/2006 | |
| WO | 2008006718 A2 | | 1/2008 | |
| WO | 2008061187 A1 | | 5/2008 | |
| WO | 2008119841 A2 | | 10/2008 | |
| WO | 2008133982 A2 | | 11/2008 | |
| WO | 2009097346 A2 | | 8/2009 | |
| WO | 2009118083 A2 | | 10/2009 | |
| WO | 2009146800 A2 | | 12/2009 | |
| WO | 2011002929 A1 | | 1/2011 | |
| WO | 2011023582 A2 | | 3/2011 | |
| WO | 2011047420 A1 | | 4/2011 | |
| WO | 2011047422 A1 | | 4/2011 | |
| WO | 2011060099 A2 | | 5/2011 | |
| WO | 2011074133 A1 | | 6/2011 | |
| WO | 2011158026 A1 | | 12/2011 | |

OTHER PUBLICATIONS

German Search Report, dated Jan. 16, 2013, from corresponding DE application.
International Search Report, dated Jul. 31, 2013, from corresponding PCT application.

* cited by examiner

*Primary Examiner* — Irina Neagu
(74) *Attorney, Agent, or Firm* — Young & Thompson

(57) ABSTRACT

Disclosed is an antimicrobial composition that includes a) one or more C3 to C5 alkane dioles-1,3, b) one or more aromatic alcohols and c) one or more C8 to C14 alkanols. A preferred component a) is propane diol-1,3. Preferred components b) are phenoxyethanol and phenethyl alcohol. A preferred component c) is undecanol-1. Optionally, an antioxidant c) is present, which is preferably Vitamin E. In a preferred embodiment the composition is a concentrate and is suitable for the antimicrobial finishing of dermatological, cosmetic and pharmaceutical products.

7 Claims, No Drawings

MIXTURE OF NATURAL OR NATURE-IDENTICAL ALCOHOLS WITH IMPROVED EFFECTIVENESS

This application is a National Stage entry of International Application No. PCT/EP2013/063372, filed on 26 Jun. 2013, which claims priority from German Patent Application No. DE 10 2012 212 281.8, filed on 13 Jul. 2012.

BACKGROUND OF THE INVENTION

Field of the Invention

The invention relates to an antimicrobial composition. In one embodiment, the composition is in the form of a concentrate. The concentrate is used for preservation in dermatological, cosmetic and pharmaceutical products. Alternatively, the antimicrobial composition is in the form of a preserved product.

Description of the Related Art

Alcohols are widespread ingredients in dermatological, cosmetic and pharmaceutical products and are used for various purposes. Preservatives approved for cosmetics in accordance with the Cosmetics Ordinance are e.g. the aromatic alcohols phenoxyethanol, benzyl alcohol and phenoxypropanol.

In cosmetic preparations, however, microbiological stabilizers are being used to an ever greater extent instead of conventional preservatives. These substances are characterized by properties such as good skin compatibility, comparatively weak microbiological effectiveness and toxicological acceptability. A large number of alcohols are used as microbiological stabilizers in various products.

In addition to the aforementioned properties, numerous manufacturers of cosmetic preparations expect the substances used to be of natural origin or nature-identical. Moreover, the odour should not be perceived as troublesome when using natural substances.

On account of this multitude of aspects, low-odour, naturally occurring toxicologically acceptable alcohols and mixtures of alcohols with good antimicrobial effectiveness are sought.

Moreover, the product Euxyl® K 350 from Schülke & Mayr GmbH is known which is in the form of a concentrate and comprises phenoxyethanol, 1,2-propylene glycol, 1-(2-ethylhexyl)glycerol, ethylparaben (ethyl p-hydroxybenzoate) and methylparaben. However, preservative concentrates, which inevitably introduce parabens into a product to be preserved, are not preferred on account of the alleged allergic potential of parabens.

WO 2011/047420 A describes topical antimicrobial preparations with a content of $C_3$- to $C_{10}$-alkanediol which compulsorily comprise a polymer of acrolein. Acrolein is a toxic, pungent-smelling aldehyde. In cosmetic products, aldehydes are often undesired. It also cannot be ruled out that, when using the preparations, small residual amounts of acrolein are present in a commercial product or are released during storage. Moreover, the polymer has limited solubility in water and is not of natural origin.

WO 2011/002929 A1 concerns combinations of essential oils and botanical extracts with alkanediols and solvents. Inter alia, a combination of benzyl alcohol with 1,3-propanediol, octanediol and decanediol is described. Concentrates with 1,2-octanediol or 1,2-decanediol are not sufficiently stable at low temperatures. An improved effect when adding $C_8$- to $C_{14}$-alkanol, as has been found according to the present invention, is not disclosed in WO 2011/002929 A1.

DE 10 2006 051 891 relates to mouth rinse solutions with a content of a) octenidine and b) non-ionic surfactant. Furthermore, c) aromatic alcohol and d) polyol are present.

WO 2008/119841 A2 describes combinations of a) at least one benzyl alcohol with b) one or more 1,2-alkanediols.

WO 2011/023582 A2 concerns the use of branched or relatively long-chain or cyclic 1,3-diols as biocides.

WO 2006/134160 A2 describes combinations of tropolones with aromatic alcohols, which are said to be antimicrobial.

SUMMARY OF THE INVENTION

The object of the present invention is therefore to provide compositions, specifically in particular in the form of a concentrate which is suitable for the antimicrobial finishing of dermatological, cosmetic and pharmaceutical products. The compositions are to be toxicologically acceptable and preferably based on natural or nature-identical constituents. They should have a very good, but at least sufficiently good, microbiological effectiveness and preferably be liquid at room temperature and stable at low temperatures and acceptable in terms of odour. Moreover, compositions, in particular in the form of a concentrate, should be suitable as carrier liquid and optionally booster for cosmetic or other antimicrobial active ingredients and functional additives.

Surprisingly, it has now been found that these and other objects are achieved by a composition which comprises
 a) one or more $C_3$- to $C_5$-1,3-alkanediols,
 b) one or more aromatic alcohols and
 c) one or more $C_8$- to $C_{14}$-alkanols.

DETAILED DESCRIPTION OF THE INVENTION

As is evident from the examples of the present application, the components a) to c) of the composition are synergistically effective.

1. Composition a) Alkanediol

The 1,3-alkanediol used according to the invention (or the optionally two or more 1,3-alkanediols) concerns those with a linear $C_3$- to $C_5$-alkyl chain.

Moreover, the 1,3-alkanediol is preferably selected from propanediols and butanediols, where 1,3-propanediol is particularly preferred.

In all embodiments of the invention, 1,3-propanediol is thus particularly preferred as component a). Compared with 1,2-propanediol, 1,3-propanediol exhibits better microbiological effectiveness and is of natural origin.

b) Aromatic Alcohol

The aromatic alcohol (or the optionally two or more aromatic alcohols) is preferably (i) aryloxyalkanol (i.e. glycol monoaryl ether) or (ii) arylalkanol.

Preferred aryloxyalkanols (i) are selected from phenoxyethanol and phenoxypropanol, preferably phenoxyethanol.

Preferred arylalkanols (ii) are selected from 3-phenyl-1-propanol, phenethyl alcohol, veratryl alcohol, benzyl alcohol or 2-methyl-1-phenyl-2-propanol, preferably 3-phenyl-1-propanol, phenethyl alcohol, veratryl alcohol or 2-methyl-1-phenyl-2-propanol, in particular phenethyl alcohol.

In all embodiments of the invention, it is preferred for the aromatic alcohol to be selected from benzyl alcohol, phenoxyethanol and phenethyl alcohol; in particular, phenethyl alcohol or phenoxyethanol are preferred as component b).

In one embodiment of the invention, the aromatic alcohol is not benzyl alcohol because, under certain circumstances, it can result, depending on the time, in the development of odour as a consequence of the formation of benzaldehyde (because benzyl alcohol is oxidation-sensitive). In one embodiment of the invention, the composition according to the invention is therefore free from benzyl alcohol. In an alternative embodiment, if benzyl alcohol is present, one (or more) other, i.e. different from benzyl alcohol, aromatic alcohol(s) is (are) moreover also present.

c) $C_8$- to $C_{14}$-Alkanol

The $C_8$- to $C_{14}$-alkanols used according to the invention are alcohols with a linear $C_8$- to $C_{14}$-alkyl chain. At a higher chain length, the solubility in water decreases, and at a lower chain length the odour becomes stronger. Preferably, the alkanol c) (the optionally two or more alkanols) is (are) selected from $C_{10}$- to $C_{12}$-alkanols, preferably undecanol, decanol or dodecanol, where undecanol is particularly preferred.

In this connection, it is preferred for the alkanol c) to be a 1-alkanol. This means that 1-undecanol is particularly preferred as component c) in all embodiments of the invention.

2. Concentrate

In a first embodiment of the invention, the composition is in the form of a concentrate. The concentrate comprises
  a) 10 to 90% by weight, preferably 20 to 80% by weight, in particular 30 to 70% by weight, such as 40 to 60% by weight, of $C_3$- to $C_5$-1,3,-alkanediol
  b) 5 to 60% by weight, preferably 10 to 55% by weight, in particular 20 to 50% by weight, such as 25 to 45% by weight, of aromatic alcohol and
  c) 1 to 50% by weight, preferably 2 to 40% by weight, in particular 3 to 30% by weight, such as 5 to 25% by weight, of $C_8$- to $C_{14}$-alkanol.

In a preferred embodiment, the concentrate comprises
  a) 20 to 80% by weight, more preferably 30 to 70% by weight, in particular 40 to 60% by weight, such as about 50% by weight, of 1,3-propanediol,
  b) 10 to 55% by weight, more preferably 20 to 50% by weight, in particular 25 to 45% by weight, such as about 35% by weight, of phenethyl alcohol and
  c) 2 to 40% by weight, more preferably 3 to 30% by weight, in particular 5 to 25% by weight or 10 to 20% by weight, such as about 15% by weight, of 1-undecanol.

Optional constituents additionally present in the composition (in particular the concentrate) are typically antioxidants such as e.g. BHA, BHT or vitamin E, particularly preferably vitamin E. Preferably, the concentrate comprises 5-1000, in particular 10-500, such as 50-100 ppm, of alpha-tocopherol (vitamin E) in order to minimize the formation of undesired degradation products. Thus, a particularly preferred concentrate consists of the components a), b) and c) and the stated small amount of antioxidant, i.e. comprises moreover no further constituents.

3. Preserved Product

Alternatively, the composition can be present in the form of a preserved product. It then comprises preferably the components a), b) and c) in a total amount (i.e. sum of the amounts of all constituents of component a), all constituents of component b) and all constituents of component c)) of 0.1 to 10% by weight, preferably 0.2 to 5% by weight, in particular 0.3 to 3% by weight, such as 0.5 to 2% by weight, based on the product.

In a further aspect, the invention relates to a use of the concentrate for preserving dermatological, cosmetic and pharmaceutical products.

Besides the obligatorily prescribed constituents a), b) and c), compositions according to the invention can moreover also comprise additives. These additives can be incorporated into the concentrates according to the invention or they are present in the cosmetic preparations, e.g. added in a targeted manner or as transfer from precursor-products. Examples are: alkyl glycerol ethers such as 1-(2-ethylhexyl)glycerol ether (Sensiva® SC 50), antioxidants such as vitamin E or derivatives thereof, complexing agents such as EDTA or salts thereof, solvents such as water (preferred), lower alcohols, alkanediols such as $C_6$-$C_{10}$ alkanediols: e.g. 1,2-hexanediol, 1,2-octanediol (preferred), 1,2-decanediol, fragrances, plant extracts, natural substances, substances of biogenic origin, antimicrobial active ingredients such as quaternary ammonium salts, e.g. benzalkonium chloride, benzethonium chloride, Vantocil IB, octenidine, LAE salts, chlorhexidine salts, isothiazolones such as MIT, BIT, OIT, carboxylic acids (and salts thereof) such as benzoic acid, sorbic acid, salicylic acid, undecylenic acid, citric acid, lactic acid, glycolic acid, formic acid, formaldehyde depot compounds such as bronopol, DMDMH, TMAD, organohalogen compounds such as bronopol, IPBC, CMI, phenols such as parabens (e.g. methylparaben, ethylparaben), cosmetic active ingredients such as Zn pyrithione, octopirox, $H_2O_2$, acids, alkalizing agents, buffers, skin moisturizers, skin care additives such as panthenol, amino acids such as arginine, acylamino acids such as Lipacide C8G, anionic surfactants, nonionic surfactants, amphoteric surfactants, quats and polymers.

Preferably, the compositions according to the invention are free from organohalogen compounds and parabens.

On account of the toxicological acceptability, the compositions according to the invention, in particular concentrates, can be used in particular in dermatological, cosmetic and pharmaceutical products. Accordingly, the use formulations according to the invention can be dermatological, cosmetic or pharmaceutical products. Such dermatological, cosmetic or pharmaceutical products are, for example, skin care preparations, preparations for wet wipes, cosmetics for sensitive skin, anti-acne compositions, sunscreen preparations, oral preparations such as, for example, mouth rinse solutions, mouthwashes, toothpastes or compositions to fight bad breath, or other compositions for antibacterial oral hygiene, compositions for hair treatment such as, for example, antidandruff compositions, cosmetics based on or partially based on natural raw materials, antiseptics, antimicrobial washing lotions, antimicrobially finished lubricants, stabilizers for cosmetic and/or pharmaceutical preparations and baby products. Preferred applications of the compositions according to the invention are the microbial stabilization of water-containing compositions such as leave-on or rinse-off products, the antimicrobial finishing of polymeric materials such as wipes, and also the boosting of the effectiveness of known antimicrobial active ingredients.

EXAMPLES

Method A—Determination of the Preserving Effect of Chemical Preservatives in Cosmetic Formulations (Koko Test)

The test described below is carried out to determine the preserving effect of chemical preservatives in cosmetic formulations.

Principle

Using the described method, the aim is to test the effectiveness of chemical preservatives with regard to the pack preservation for cosmetic formulations. For this purpose, the preservatives to be tested are added in various concentrations to the unpreserved samples in different experimental batches. A continuous microbial burden is achieved by periodically inoculating the experimental batches. In parallel to the inoculation, streaks of the individual batches are in each case made immediately beforehand. Assessment is made by reference to the microbial growth of the streaks. The longer the period before the first appearance of microbial growth, the more effective the preservative.

Procedure

In each case, 25 g of the cosmetic to be tested are weighed into wide-necked bottles with screw closure (LDPE). The preservatives to be tested are added in their use concentrations in separate batches in each case. (Samples which have been sent for testing in an already preserved form receive no further addition of biocide.) Serving as growth control in each case is an unpreserved specimen. Two days after adding the preservative, the samples are infected with 0.1 ml of an inoculation solution consisting of the test organisms listed below. The inoculation solution has a titre of about $10^8$-$10^9$ germs/ml.

| Bacteria | Gram-positive | | Staphylococcus aureus | ATCC 6538 |
|---|---|---|---|---|
| | | | Kocuria rhizophila | ATCC 9341 |
| | Gram-negative | Enterobacteria | Enterobacter gergoviae | ATCC 33028 |
| | | | Escherichia coli | ATCC 11229 |
| | | | Klebsiella pneumoniae | ATCC 4352 |
| | | Pseudomonads | Pseudomonas aeruginosa | ATCC 9027 |
| | | | Pseudomonas fluorescens | ATCC 17397 |
| | | | Pseudomonas putida | ATCC 12633 |
| Yeast | | | Candida albicans | ATCC 10231 |
| Moulds | | | Aspergillus brasiliensis | ATCC 16404 |
| | | | Penicillium pinophilum | ATCC 36839 |

The test batches are subsequently inoculated once a week and streaked onto agar plates once a week (casein peptone-soya flour peptone agar (CSA) for bacteria and Sabouraud dextrose agar (SA) for yeasts and moulds), the first streak (sterility test) being made both on disinhibited (TLSH) and also on non-disinhibited nutrient media in order, as far as possible, to reveal all starting contaminations. Assessment of the microbial growth of the streaks takes place after incubation for three days at 25° C. To be on the safe side, negative streaks are observed for a further two days and reassessed. The preserving effect of the individual product concentrations is assessed in a semi-quantitative method by means of the growth of the individual streaks.

| − = growth-free | ++ = moderate growth |
|---|---|
| + = weak growth | +++ = considerable growth |

The growth is differentiated according to bacteria, yeasts and moulds. The experiment is carried out for a maximum of six weeks, i.e. over six inoculation cycles, or terminated after considerable growth (+++) on multiple occasions.

Assessment of the Results

The sample is well-preserved according to criterion A if it exists under the laboratory conditions given above for a period of six weeks without microbial attack of the sample batches, i.e. no microbial growth can be detected even after the sixth inoculation. Based on experience over many years with this test method, a microbiological stability recommended for cosmetics of more than 30 months can be inferred from this.

If the sample reveals weak microbial growth (+) during the six inoculation cycles, the sample satisfies criterion B. A B criterion can constitute adequate preservation if the microbiological risk analysis has control factors independent of the formulation. This could be e.g. the use of a packaging with pump instead of a can and/or high requirements on good manufacturing practice (GMP).

Test Results

| | Test material/product | pH | Sterility control | Inoculation cycle | | | | | |
|---|---|---|---|---|---|---|---|---|---|
| | | | | 1 | 2 | 3 | 4 | 5 | 6 |
| 1 | Carbopol gel unpreserved | — | | +++ B, M, Y | +++ B, M, Y | / | | | |
| 2 | +0.5% 1,3-propanedial | — | | +++ B, M, Y | +++ B, M, Y | / | | | |
| 3 | +0.1% 1,3-propanedial | — | | +++ B, M, Y | +++ B, M, Y | / | | | |
| 4 | +0.5% phenethyl alcohol | — | | +++ B, M, Y | +++ B, M, Y | / | | | |
| 5 | +0.5% 1,3-propanedial +0.5% phenethyl alcohol | — | | +++ B, M | ++ B, M | ++ B | + B | ++ B | ++ B, M |
| 6 | +0.5% 1,3-propanedial +0.05% undecanol +0.45% phenethyl alcohol | — | | — | — | — | — | — | — |
| 7 | +0.5% 1,3-propanedial +0.15% undecanol +0.35% phenethyl alcohol | — | | — | — | — | — | — | — |
| 8 | +0.5% 1,3-propanedial +0.25% undecanol +0.25% phenethyl alcohol | — | | — | — | — | — | — | — |
| 9 | +0.5% 1,3-propanediol +0.1% undecanol | — | | +++ B, M, Y | +++ B, M, Y | / | — | — | — |
| 10 | +0.5% 1,3-propanediol +0.5% Euxyl PE 9010 | — | | +++ B, M, Y | ++ B | + B | ++ B | ++ B | ++ B |

Key: B = Bacteria
M = Moulds
Sp = Spore-forming bacterium
Y = Yeasts
/ = The test was terminated The test results reveal that 0.5 and also 1.0% by weight of 1,3-propanediol (corresponds to component a)) are not effective (Experiments 2 and 3). Also 0.5% by weight of phenethyl alcohol, corresponding to component b), is not effective by itself (Experiment 4). The same is true for the combination of 0.5% by weight of 1,3-propanediol (component a)) with 0.1% by weight of 1-undecanol (component c)), cf. Experiment 9. Example 9 reveals that 0.1% by weight of 1-undecanol leads to no improvement when added to Experiment 2 with 0.5% by weight of 1,3-propanediol. This suggests that 1-undecanol itself, at least in an amount of 0.1% by weight, also has no effect by itself.

The effect of the combination of 0.5% by weight of 1,3-propanediol with 0.5% by weight of phenethyl alcohol (Experiment 5) is very slight; the same is true for the combination of 0.5% by weight of 1,3-propanediol with 0.5% by weight of Euxyl PE 9010 (this is a mixture of 90% by weight of phenoxyethanol with 10% by weight of 1-(2-ethylhexyl)glycerol), cf. Experiment 10.

By contrast, the three-component combination according to the invention as per Experiments 6 to 8, in each case with 0.5% by weight of 1,3-propanediol, is surprisingly effective:

- in Example 6, 10 parts by weight of 1,3-propanediol, 9 parts by weight of phenethyl alcohol and 1 part by weight of 1-undecanol (in a total amount of 1.0% by weight) are used,
- in Example 7, 10 parts by weight of 1,3-propanediol, 7 parts by weight of phenethyl alcohol and 3 parts by weight of 1-undecanol (in a total amount of 1.0% by weight) are used, and
- in Example 8, 10 parts by weight of 1,3-propanediol, 5 parts by weight of phenethyl alcohol and 5 parts by weight of 1-undecanol (in a total amount of 1.0% by weight) are used.

The invention claimed is:

1. An antimicrobial composition in the form of a concentrate, which comprises:
    a) 20 to 80% by weight of 1,3-propanediol,
    b) 10 to 55% by weight of phenethyl alcohol and
    c) 2 to 40% by weight of 1-undecanol.

2. The antimicrobial composition in the form of a concentrate according to claim 1, which comprises:
    a) 30 to 70% by weight of 1,3-propanediol,
    b) 20 to 50% by weight of phenethyl alcohol and
    c) 3 to 30% by weight of 1-undecanol.

3. The antimicrobial composition in the form of a concentrate according to claim 2, which comprises:
    a) 40 to 60% by weight of 1,3-propanediol,
    b) 25 to 45% by weight of phenethyl alcohol and
    c) 5 to 25% by weight of 1-undecanol.

4. The antimicrobial composition in the form of a concentrate according to claim 1, which further comprises 5-1000 ppm of alpha-tocopherol (vitamin E).

5. The antimicrobial composition in the form of a concentrate according to claim 2, which further comprises 5-1000 ppm of alpha-tocopherol (vitamin E).

6. The antimicrobial composition in the form of a concentrate according to claim 3, which further comprises 5-1000 ppm of alpha-tocopherol (vitamin E).

7. A method for preserving dermatological, cosmetic or pharmaceutical products, comprising
    treating said dermatological, cosmetic or pharmaceutical products with the antimicrobial composition in the form of a concentrate according to claim 1.

* * * * *